(12) United States Patent
Cao et al.

(10) Patent No.: US 11,825,201 B2
(45) Date of Patent: Nov. 21, 2023

(54) IMAGE SENSORS AND METHODS OF OPERATING THE SAME

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/859,424

(22) Filed: Jul. 7, 2022

(65) Prior Publication Data

US 2022/0345627 A1    Oct. 27, 2022

Related U.S. Application Data

(63) Continuation of application No. PCT/CN2020/076786, filed on Feb. 26, 2020.

(51) Int. Cl.
*H04N 23/698* (2023.01)
*G06T 3/40* (2006.01)
*H04N 23/695* (2023.01)

(52) U.S. Cl.
CPC ......... *H04N 23/698* (2023.01); *G06T 3/4038* (2013.01); *H04N 23/695* (2023.01)

(58) Field of Classification Search
CPC .. H04N 5/23238; H04N 5/23299; H04N 5/32; H04N 5/265; H04N 5/2258; G06T 3/4038; H01L 27/14603; H01L 27/14636
See application file for complete search history.

(56) References Cited

U.S. PATENT DOCUMENTS

| | | | | |
|---|---|---|---|---|
| 6,273,606 B1 * | 8/2001 | Dewaele | ............... | A61B 6/5241 |
| | | | | 378/98.12 |
| 6,483,893 B1 * | 11/2002 | Achtnig | ................. | G01N 23/04 |
| | | | | 378/98.12 |

(Continued)

FOREIGN PATENT DOCUMENTS

| CN | 109414231 A | 3/2019 |
|---|---|---|
| CN | 109906388 A | 6/2019 |

(Continued)

*Primary Examiner* — Michael Lee
(74) *Attorney, Agent, or Firm* — IPRO, PLLC; Qian Gu

(57) ABSTRACT

Disclosed herein is a method of using an image sensor comprising N sensing areas for capturing images of a scene, the N sensing areas being physically separate from each other, the method comprising: for i=1, . . . , P, and j=1, . . . , Q(i), positioning the image sensor at a location (i,j) and capturing a partial image (i,j) of the scene using the image sensor while the image sensor is at the location (i,j), thereby capturing in total R partial images, wherein R is the sum of Q(i), i=1, . . . , P, wherein P>1, wherein Q(i), i=1, . . . , P are positive integers and are not all 1, wherein for i=1, . . . , P, a location group (i) comprises the locations (i,j), j=1, . . . , Q(i), and wherein a minimum distance between 2 locations of 2 different location groups is substantially larger than a maximum distance between two locations of a same location group; and determining a combined image of the scene based on the R partial images.

54 Claims, 9 Drawing Sheets

(56) References Cited

U.S. PATENT DOCUMENTS

| | | | |
|---|---|---|---|
| 6,793,390 B2 * | 9/2004 | Wang | G06T 3/0075 |
| | | | 378/174 |
| 2007/0023669 A1 | 2/2007 | Hefetz et al. | |
| 2010/0014780 A1 * | 1/2010 | Kalayeh | G06T 7/33 |
| | | | 382/284 |
| 2010/0225837 A1 | 9/2010 | Seki et al. | |
| 2014/0086394 A1 * | 3/2014 | Batkilin | G01T 7/005 |
| | | | 378/207 |
| 2017/0084052 A1 * | 3/2017 | Olsson | H04N 5/2257 |
| 2017/0325761 A1 * | 11/2017 | Wojcik | A61B 90/39 |
| 2018/0139364 A1 * | 5/2018 | Jannard | H04N 13/189 |
| 2019/0069858 A1 * | 3/2019 | Cao | A61B 6/54 |
| 2019/0216415 A1 * | 7/2019 | Wojcik | A61B 6/4283 |
| 2019/0335099 A1 * | 10/2019 | Zhang | H04N 5/23238 |
| 2020/0237332 A1 * | 7/2020 | Wang | A61B 6/5241 |
| 2020/0345322 A1 * | 11/2020 | Bai | A61B 6/4266 |
| 2021/0169434 A1 * | 6/2021 | Cao | G01V 5/0066 |
| 2021/0172887 A1 * | 6/2021 | Cao | H04N 5/32 |
| 2021/0185203 A1 * | 6/2021 | Cao | A61B 6/4452 |
| 2021/0239861 A1 * | 8/2021 | Cao | G01V 5/0066 |
| 2021/0321962 A1 * | 10/2021 | Wang | G01T 1/24 |
| 2021/0325319 A1 * | 10/2021 | Cao | G01T 1/16 |
| 2021/0405222 A1 * | 12/2021 | Cao | A61B 6/06 |
| 2021/0407133 A1 * | 12/2021 | Liu | G06T 3/0006 |
| 2022/0349841 A1 * | 11/2022 | Cao | G01N 23/041 |
| 2022/0350038 A1 * | 11/2022 | Liu | G01T 1/17 |

FOREIGN PATENT DOCUMENTS

| | | |
|---|---|---|
| DE | 102012203291 A1 | 3/2013 |
| JP | 2004362905 A | 12/2004 |
| TW | 200942854 A | 10/2009 |

* cited by examiner

710: Capturing partial images of the scene at different image capture locations.

720: Stitching some partial images (one from each partial image group) to form a stitched image of the scene.

730: Determining enhanced partial images and using them to enhance the stitched image.

740: Equalizing resolutions of the stitched image if necessary.

810: positioning the image sensor 490 at different locations and capturing different partial images of a same scene with the image sensor 490 are at these locations, wherein a minimum distance between two locations of two different location groups is substantially larger than a maximum distance between two locations of a location group.

820: determining a combined image of the scene based on the captured partial images.

FIG. 8

IMAGE SENSORS AND METHODS OF OPERATING THE SAME

TECHNICAL FIELD

The disclosure herein relates to image sensors and methods of operating the same.

BACKGROUND

A radiation detector is a device that measures a property of a radiation. Examples of the property may include a spatial distribution of the intensity, phase, and polarization of the radiation. The radiation may be one that has interacted with an object. For example, the radiation measured by the radiation detector may be a radiation that has penetrated the object. The radiation may be an electromagnetic radiation such as infrared light, visible light, ultraviolet light, X-ray or γ-ray. The radiation may be of other types such as α-rays and β-rays. An image sensor may include multiple radiation detectors. The radiation may include radiation particles such as photons (i.e., electromagnetic waves) and subatomic particles.

SUMMARY

Disclosed herein is a method of using an image sensor comprising N sensing areas for capturing images of a scene, N being a positive integer, the N sensing areas being physically separate from each other, the method comprising: for i=1, ..., P, and j=1, ..., Q(i), positioning the image sensor at a location (i,j) relative to the scene and capturing a partial image (i,j) of the scene using the image sensor while the image sensor is at the location (i,j), thereby capturing in total R partial images, wherein R is the sum of Q(i), i=1, ..., P, wherein P is an integer greater than 1, wherein Q(i), i=1, ..., P are positive integers and are not all 1, wherein for i=1, ..., P, a location group (i) comprises the locations (i,j), j=1, ..., Q(i), and wherein a minimum distance between a location of a location group of the location groups (i), i=1, ..., P and another location of another location group of the location groups (i), i=1, ..., P is substantially larger than a maximum distance between two locations of a location group of the location groups (i), i=1, ..., P; and determining a combined image of the scene based on the R partial images.

According to an embodiment, N is greater than 1.

According to an embodiment, said positioning the image sensor at the locations (i,j) for i=1, ..., P, and j=1, ..., Q(i) are performed one by one.

According to an embodiment, Q(i), i=1, ..., P are the same and greater than 1.

According to an embodiment, said minimum distance is close to and less than a size of a sensing area of the N sensing areas.

According to an embodiment, said minimum distance is more than 100 times said maximum distance.

According to an embodiment, said maximum distance is less than 10 times a size of a sensing element of the N sensing areas.

According to an embodiment, said positioning the image sensor at the locations (i,j) for i=1, ..., P, and j=1, ..., Q(i) comprises moving the image sensor from a location of a location group of the location groups (i), i=1, ..., P directly to another location of another location group of the location groups (i), i=1, ..., P and does not comprise moving the image sensor from a location of a location group of the location groups (i), i=1, ..., P directly to another location of the same location group.

According to an embodiment, said determining the combined image comprises stitching the partial images (i,1), i=1, ..., P to form a stitched image of the scene.

According to an embodiment, said determining the combined image further comprises for i=1, ..., P determining an enhanced partial image (i) based on the partial images (i,j), j=1, ..., Q(i).

According to an embodiment, said determining the combined image further comprises for i=1, ..., P using the enhanced partial image (i) to replace the partial image (i,1) of the stitched image.

According to an embodiment, said determining the combined image further comprises equalizing resolutions of different regions of the stitched image after said using is performed.

According to an embodiment, said determining the combined image further comprises for i=1, ..., P using the enhanced partial image (i) to replace the partial image (i,1) of the stitched image if a resolution of the enhanced partial image (i) is higher than that of the partial image (i,1).

According to an embodiment, said determining the enhanced partial images (i) comprises determining positions of the locations (i,j), j=1, ..., Q(i) relative to each other.

According to an embodiment, said determining the positions of the locations (i,j), j=1, ..., Q(i) relative to each other comprises using markers which are stationary relative to the scene.

According to an embodiment, said determining the positions of the locations (i,j), j=1, ..., Q(i) relative to each other comprises: upsampling the partial images (i,j), j=1, ..., Q(i) resulting in upsampled partial images (i,j), j=1, ..., Q(i) respectively; and correlating the upsampled partial images (i,j), j=1, ..., Q(i) to determine the positions of the locations (i,j), j=1, ..., Q(i) relative to each other.

According to an embodiment, said determining the combined image comprises for i=1, ..., P determining an enhanced partial image (i) based on the partial images (i,j), j=1, ..., Q(i).

According to an embodiment, said determining the combined image further comprises stitching the enhanced partial images (i), i=1, ..., P to form a stitched image of the scene.

According to an embodiment, said determining the combined image further comprises equalizing resolutions of different regions of the stitched image.

BRIEF DESCRIPTION OF FIGURES

FIG. 7 shows a flowchart summarizing the operation of the image sensor, according to an embodiment.

FIG. 8 shows another flowchart summarizing and generalizing an operation of the image sensor, according to an embodiment.

DETAILED DESCRIPTION

Figure 1:
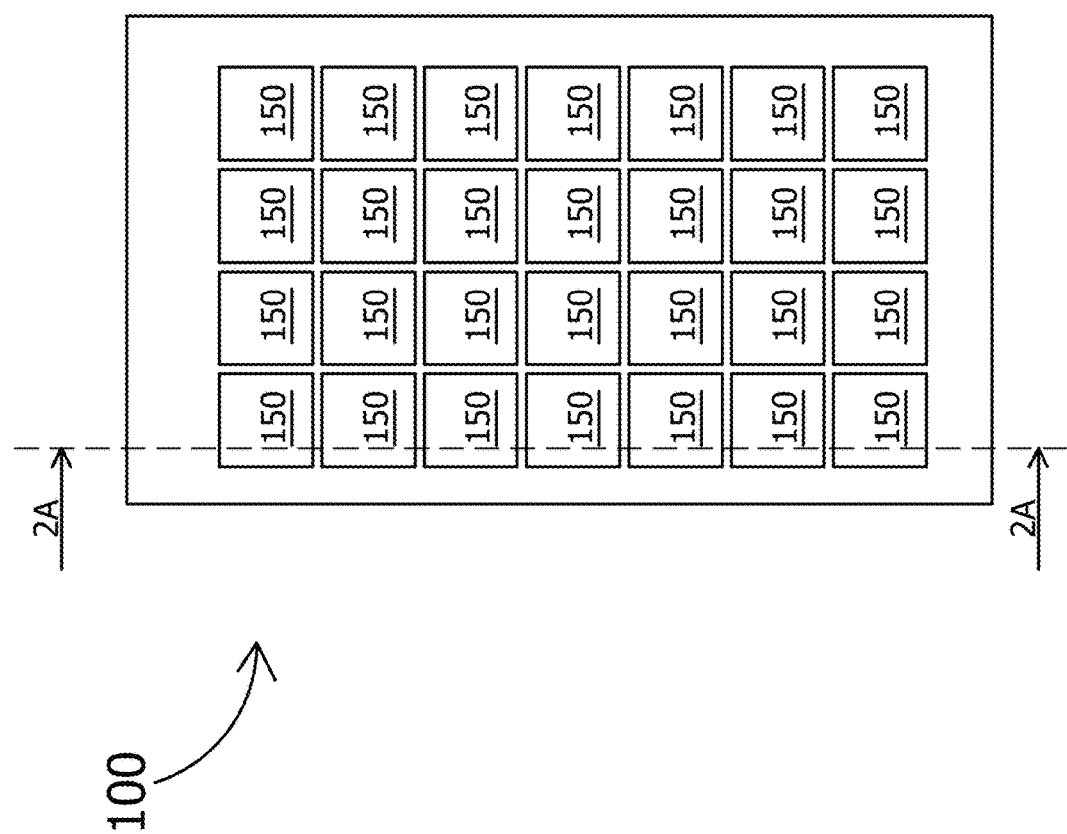
FIG. 1 schematically shows a radiation detector, according to an embodiment.

FIG. 1 schematically shows a radiation detector 100, as an example. The radiation detector 100 may include an array of sensing elements 150 (also referred to as pixels 150). The array may be a rectangular array (as shown in FIG. 1), a honeycomb array, a hexagonal array or any other suitable array. The radiation detector 100 in the example of FIG. 1 has 28 sensing elements 150 arranged in 7 rows and 4 columns; however, in general, the radiation detector 100 may have any number of sensing elements 150 arranged in any way.

Each sensing element 150 may be configured to detect radiation from a radiation source (not shown) incident thereon and may be configured to measure a characteristic (e.g., the energy of the particles, the wavelength, and the frequency) of the radiation. A radiation may include particles such as photons (electromagnetic waves) and sub-atomic particles. Each sensing element 150 may be configured to count numbers of particles of radiation incident thereon whose energy falls in a plurality of bins of energy, within a period of time. All the sensing elements 150 may be configured to count the numbers of particles of radiation incident thereon within a plurality of bins of energy within the same period of time. When the incident particles of radiation have similar energy, the sensing elements 150 may be simply configured to count numbers of particles of radiation incident thereon within a period of time, without measuring the energy of the individual particles of radiation.

Each sensing element 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The sensing elements 150 may be configured to operate in parallel. For example, when one sensing element 150 measures an incident particle of radiation, another sensing element 150 may be waiting for a particle of radiation to arrive. The sensing elements 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

Figure 2A:
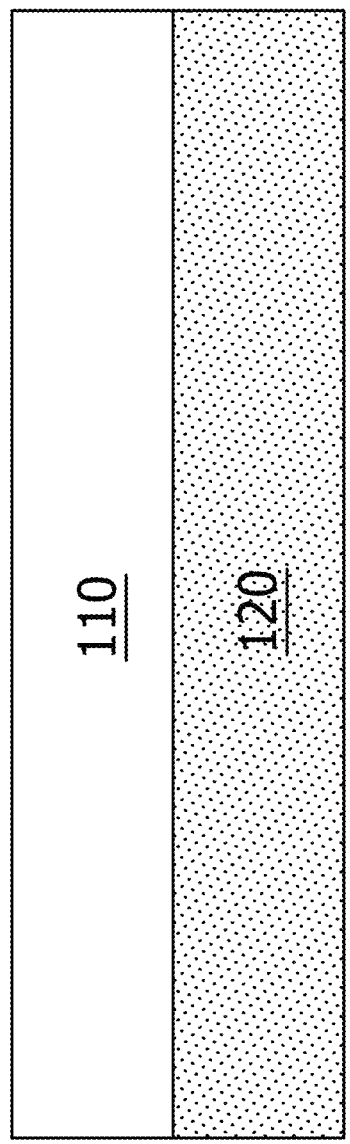
FIG. 2A schematically shows a simplified cross-sectional view of the radiation detector.

FIG. 2A schematically shows a simplified cross-sectional view of the radiation detector 100 of FIG. 1 along a line 2A-2A, according to an embodiment. More specifically, the radiation detector 100 may include a radiation absorption layer 110 and an electronics layer 120 (e.g., an ASIC) for processing or analyzing electrical signals which incident radiation generates in the radiation absorption layer 110. The radiation detector 100 may or may not include a scintillator (not shown). The radiation absorption layer 110 may comprise a semiconductor material such as, silicon, germanium, GaAs, CdTe, CdZnTe, or a combination thereof. The semiconductor material may have a high mass attenuation coefficient for the radiation of interest.

Figure 2B:
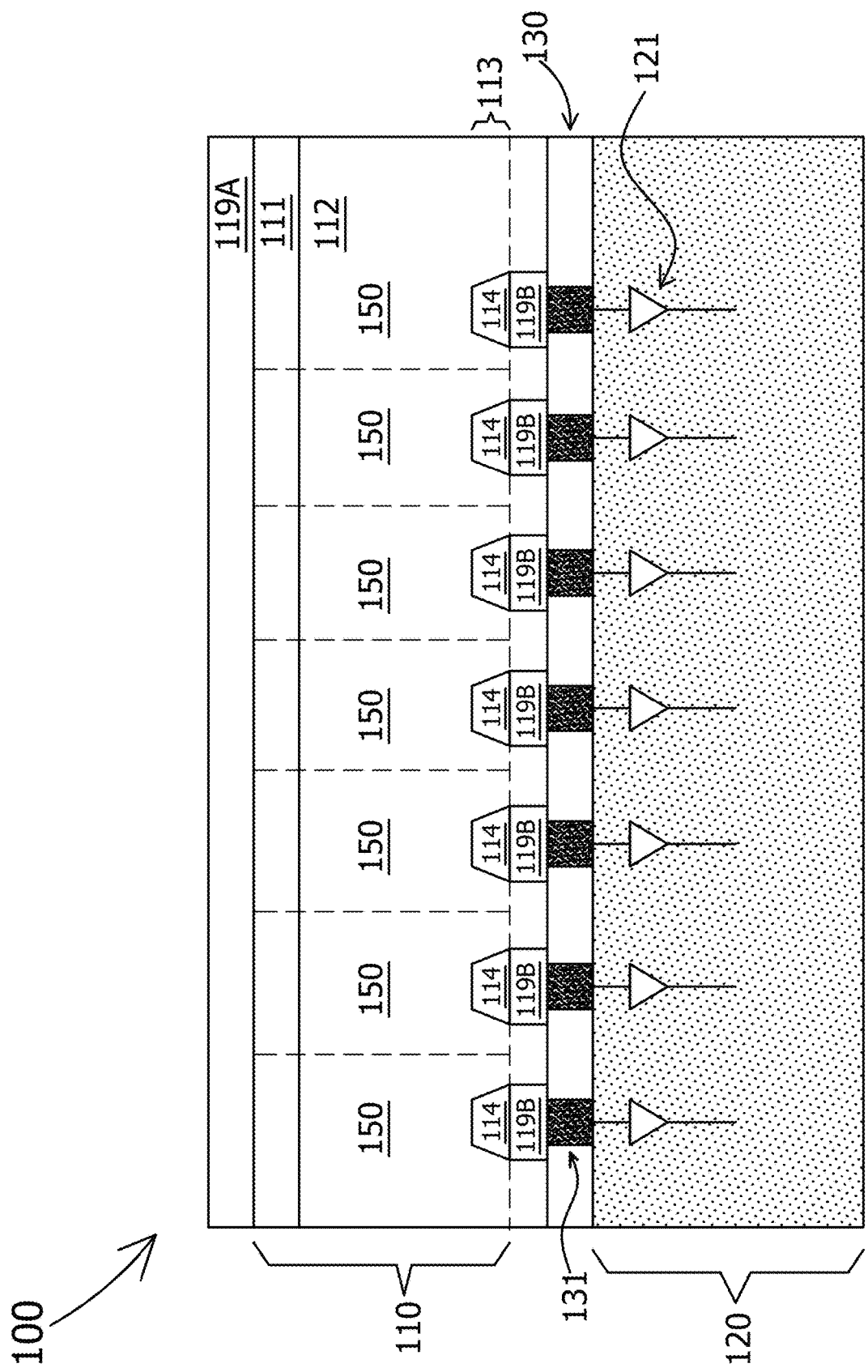
FIG. 2B schematically shows a detailed cross-sectional view of the radiation detector.

FIG. 2B schematically shows a detailed cross-sectional view of the radiation detector 100 of FIG. 1 along the line 2A-2A, as an example. More specifically, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example of FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes (more specifically, 7 diodes corresponding to 7 sensing elements 150 of one row in the array of FIG. 1). The plurality of diodes have an electrode 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs. The electronic system 121 may include components shared by the sensing elements 150 or components dedicated to a single sensing element 150. For example, the electronic system 121 may include an amplifier dedicated to each sensing element 150 and a microprocessor shared among all the sensing elements 150. The electronic system 121 may be electrically connected to the sensing elements 150 by vias 131. Space among the vias may be filled with a filler material 130, which may increase the mechanical stability of the connection of the electronics layer 120 to the radiation absorption layer 110. Other bonding techniques are possible to connect the electronic system 121 to the sensing elements 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A sensing element 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the sensing element 150.

Figure 2C:
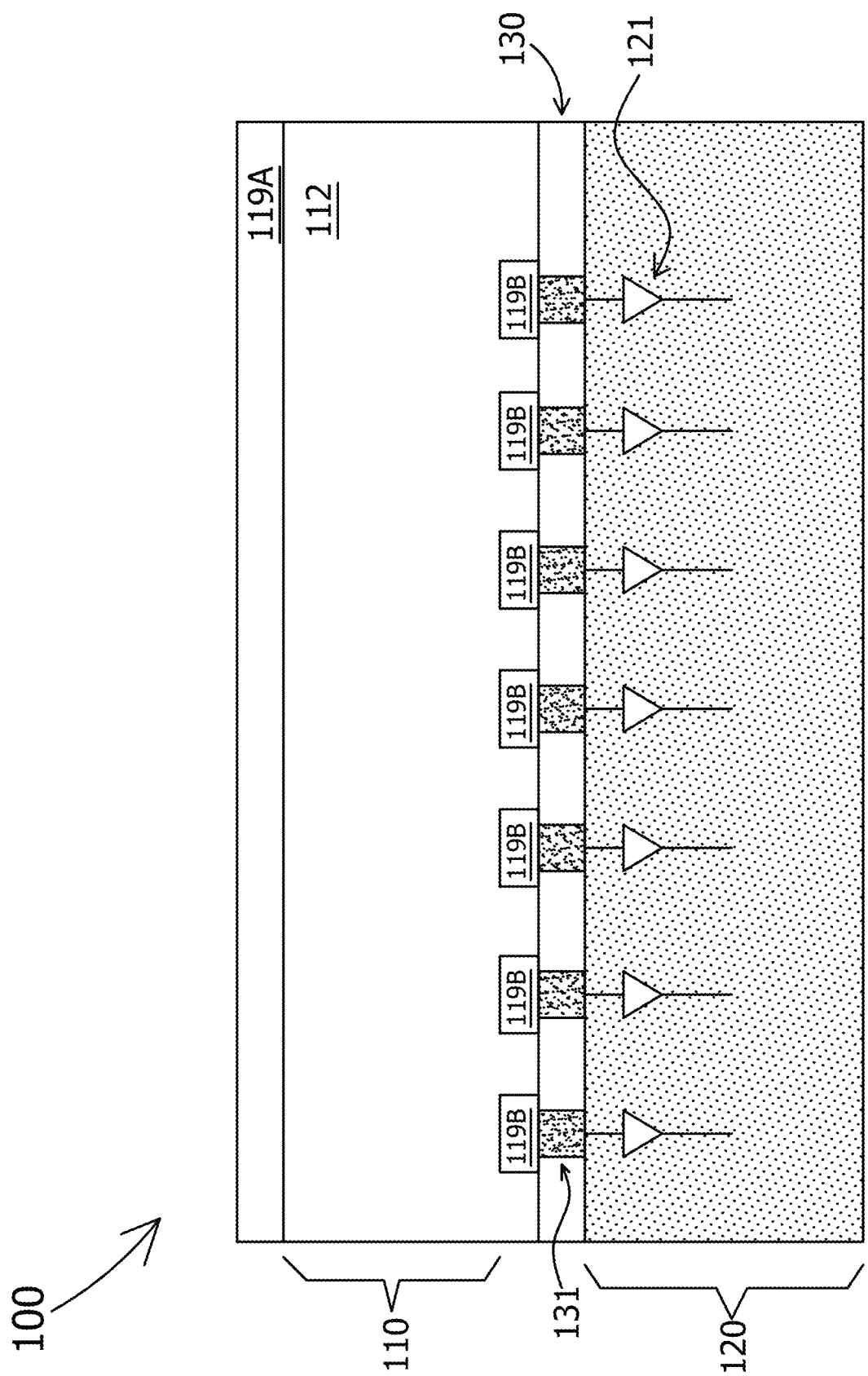
FIG. 2C schematically shows an alternative detailed cross-sectional view of the radiation detector.

FIG. 2C schematically shows an alternative detailed cross-sectional view of the radiation detector 100 of FIG. 1 along the line 2A-2A, according to an embodiment. More specifically, the radiation absorption layer 110 may include a resistor of a semiconductor material such as, silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 2C is similar to the electronics layer 120 of FIG. 2B in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A sensing element 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the sensing element associated with the one discrete portion of the electrical contact 119B.

Figure 3:
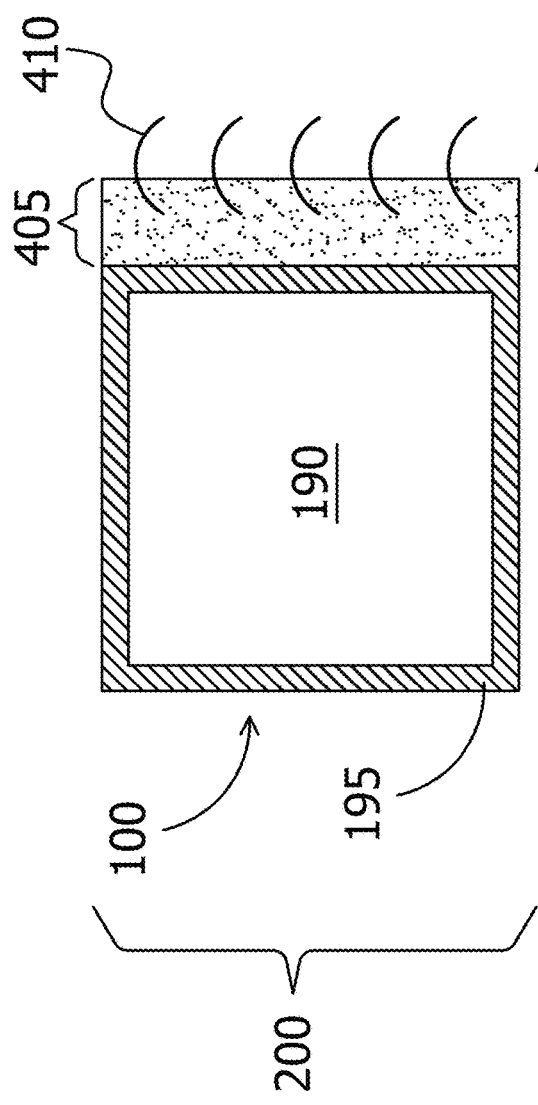
FIG. 3 schematically shows a top view of a package including the radiation detector and a printed circuit board (PCB).

FIG. 3 schematically shows a top view of a package 200 including the radiation detector 100 and a printed circuit board (PCB) 400. The term "PCB" as used herein is not limited to a particular material. For example, a PCB may include a semiconductor. The radiation detector 100 is mounted to the PCB 400. The wiring between the detector 100 and the PCB 400 is not shown for the sake of clarity. The PCB 400 may have one or more radiation detectors 100. The PCB 400 may have an area 405 not covered by the radiation detector 100 (e.g., for accommodating bonding wires 410). The radiation detector 100 may have a sensing area 190, which is where the sensing elements 150 (FIG. 1) are located. The radiation detector 100 may have a perimeter zone 195 near the edges of the radiation detector 100. The perimeter zone 195 has no sensing elements and the radiation detector 100 does not detect particles of radiation incident on the perimeter zone 195.

Figure 4:
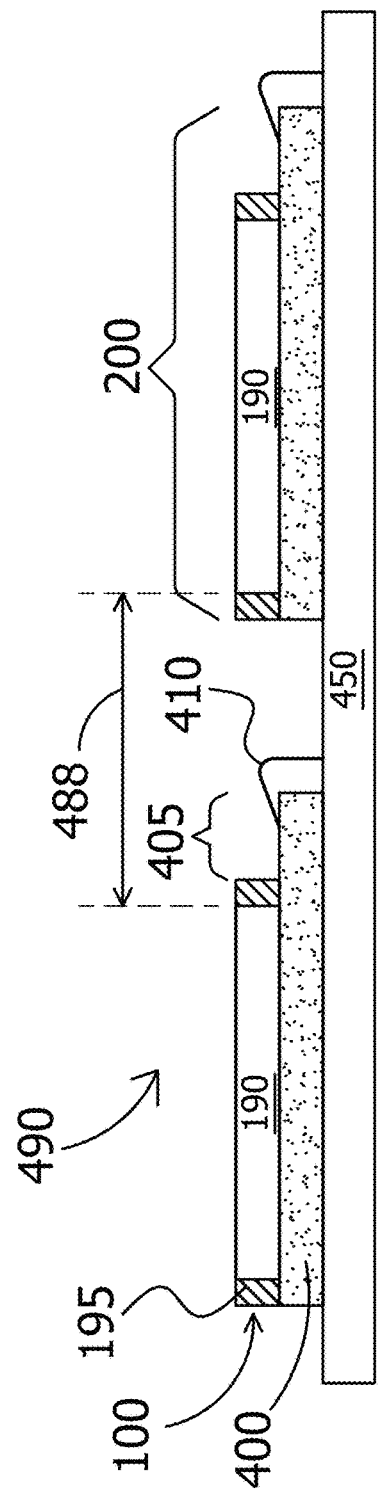
FIG. 4 schematically shows a cross-sectional view of an image sensor, where a plurality of the packages of FIG. 3 are mounted to a system PCB, according to an embodiment.

FIG. 4 schematically shows a cross-sectional view of an image sensor 490, according to an embodiment. The image sensor 490 may include a plurality of the packages 200 of FIG. 3 mounted to a system PCB 450. As an example, the image sensor 490 may include 2 packages 200 as shown in FIG. 4. The electrical connection between the PCBs 400 and the system PCB 450 may be made by bonding wires 410. In order to accommodate the bonding wires 410 on the PCB 400, the PCB 400 has the area 405 not covered by the detector 100. In order to accommodate the bonding wires 410 on the system PCB 450, the packages 200 have gaps in between. The gaps may be approximately 1 mm or more. Particles of radiation incident on the perimeter zones 195, on the area 405 or on the gaps cannot be detected by the packages 200 on the system PCB 450.

A dead zone of a radiation detector (e.g., the radiation detector 100) is the area of the radiation-receiving surface of the radiation detector, in which incident particles of radiation cannot be detected by the radiation detector. A dead zone of a package (e.g., package 200) is the area of the radiation-receiving surface of the package, in which incident particles of radiation cannot be detected by the detector or detectors in the package. In this example shown in FIG. 3 and FIG. 4, the dead zone of the package 200 includes the perimeter zones 195 and the area 405. A dead zone (e.g., 488) of an image sensor (e.g., image sensor 490) with a group of packages (e.g., packages mounted on the same PCB, packages arranged in the same layer) includes the combination of the dead zones of the packages in the group and the gaps among the packages.

In an embodiment, the image sensor 490 including the radiation detectors 100 may have the dead zone 488 incapable of detecting incident radiation. However, in an embodiment, the image sensor 490 with sensing areas 190 may capture partial images of an object or scene (not shown), and then these captured partial images may be stitched to form a full image of the object or scene.

FIG. 5A-FIG. 5D schematically show top views of the image sensor 490 in operation, according to an embodiment. For simplicity, only the 2 sensing areas 190a and 190b and the dead zone 488 of the image sensor 490 are shown (i.e., other parts of the image sensor 490 such as perimeter zones 195 (FIG. 4) are not shown). In an embodiment, a cardboard box 510 enclosing a metal sword 512 may be positioned between the image sensor 490 and a radiation source (not shown) which is before the page. The cardboard box 510 is between the image sensor 490 and the eye of viewer. Hereafter, for generalization, the cardboard box 510 enclosing the metal sword 512 may be referred to as the object/scene 510+512.

Figure 5:
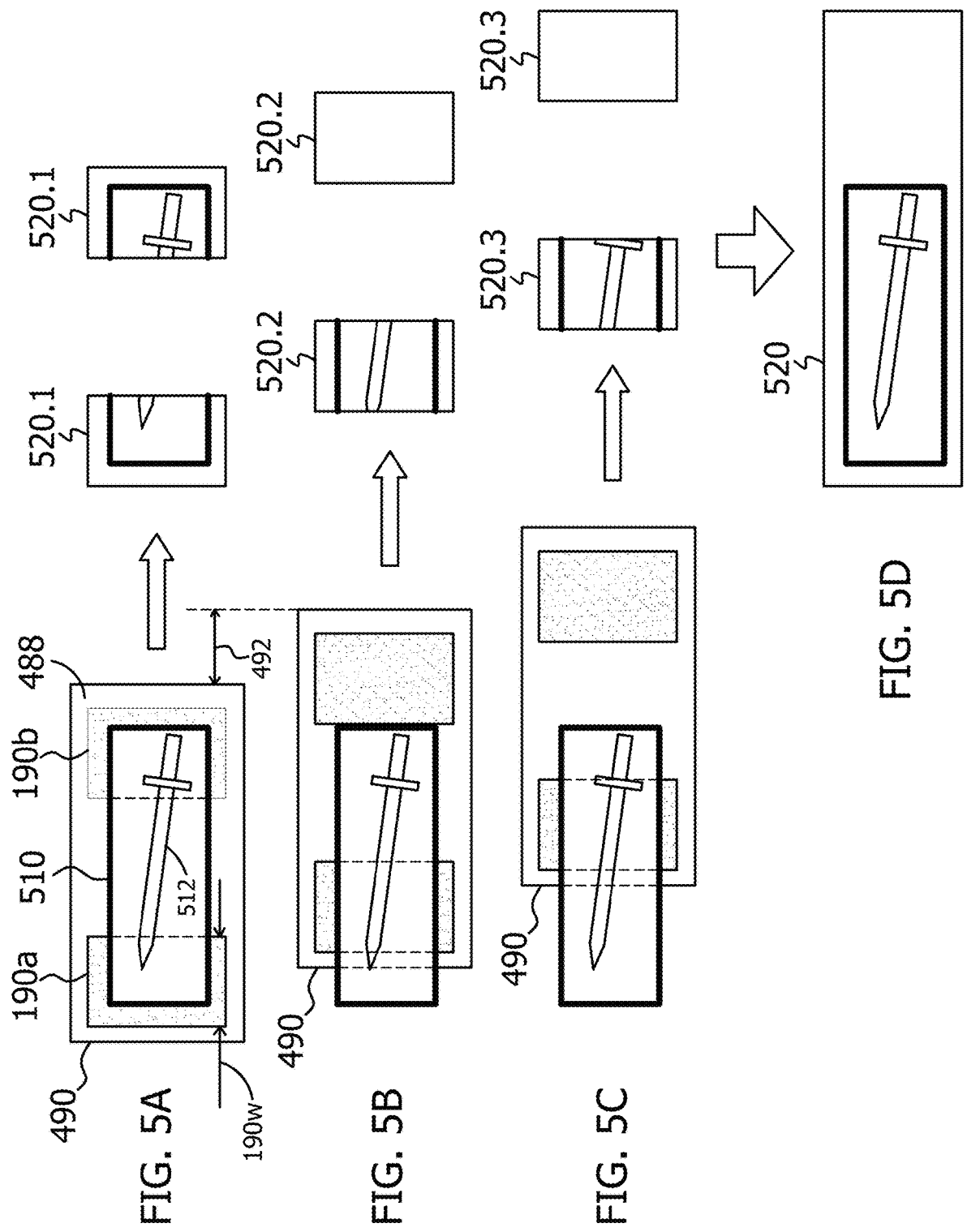
FIG. 5A-FIG. 5D schematically show top views of the image sensor in operation, according to an embodiment.

In an embodiment, the operation of the image sensor 490 in capturing images of the object/scene 510+512 may be as follows. Firstly, the object/scene 510+512 may be stationary, and the image sensor 490 may be moved to a first image capture location relative to the object/scene 510+512 as shown in FIG. 5A. Then, the image sensor 490 may be used to capture a first partial image 520.1 of the object/scene 510+512 while the image sensor 490 is at the first image capture location.

Next, in an embodiment, the image sensor 490 may be moved to a second image capture location relative to the object/scene 510+512 as shown in FIG. 5B. Then, the image sensor 490 may be used to capture a second partial image 520.2 of the object/scene 510+512 while the image sensor 490 is at the second image capture location.

Next, in an embodiment, the image sensor 490 may be moved to a third image capture location relative to the object/scene 510+512 as shown in FIG. 5C. Then, the image sensor 490 may be used to capture a third partial image 520.3 of the object/scene 510+512 while the image sensor 490 is at the third image capture location.

In an embodiment, the size and shape of the sensing areas 190a and 190b and the positions of the first, second, and third image capture locations may be such that any partial image of the partial images 520.1, 520.2, and 520.3 overlaps at least another partial image of the partial images 520.1, 520.2, and 520.3. For example, a distance 492 between the first and second image capture locations may be close to and less than a width 190w of the sensing area 190a; as a result, the first partial image 520.1 overlaps the second partial image 520.2.

In an embodiment, with any partial image of the partial images 520.1, 520.2, and 520.3 overlapping at least another partial image of the partial images 520.1, 520.2, and 520.3, the partial images 520.1, 520.2, and 520.3 may be stitched to form a more complete image 520 (FIG. 5D) of the object/scene 510+512. In an embodiment, the size and shape of the sensing areas 190a and 190b and the positions of the first, second, and third image capture locations may be such that the stitched image 520 covers the entire object/scene 510+512 as shown in FIG. 5D.

FIG. 6A-FIG. 6D schematically show top views of the image sensor 490 in operation, according to an alternative embodiment. In an embodiment, the operation of the image sensor 490 in FIG. 6A-FIG. 6D may be similar to the operation of the image sensor 490 in FIG. 5A-FIG. 5D with respect to the capturing of the partial images 520.1, 520.2, and 520.3. In an embodiment, in addition to the capturing of the partial images 520.1, 520.2, and 520.3 as described above, the operation of the image sensor 490 in FIG. 6A-FIG. 6D may further include the following.

Figure 6:
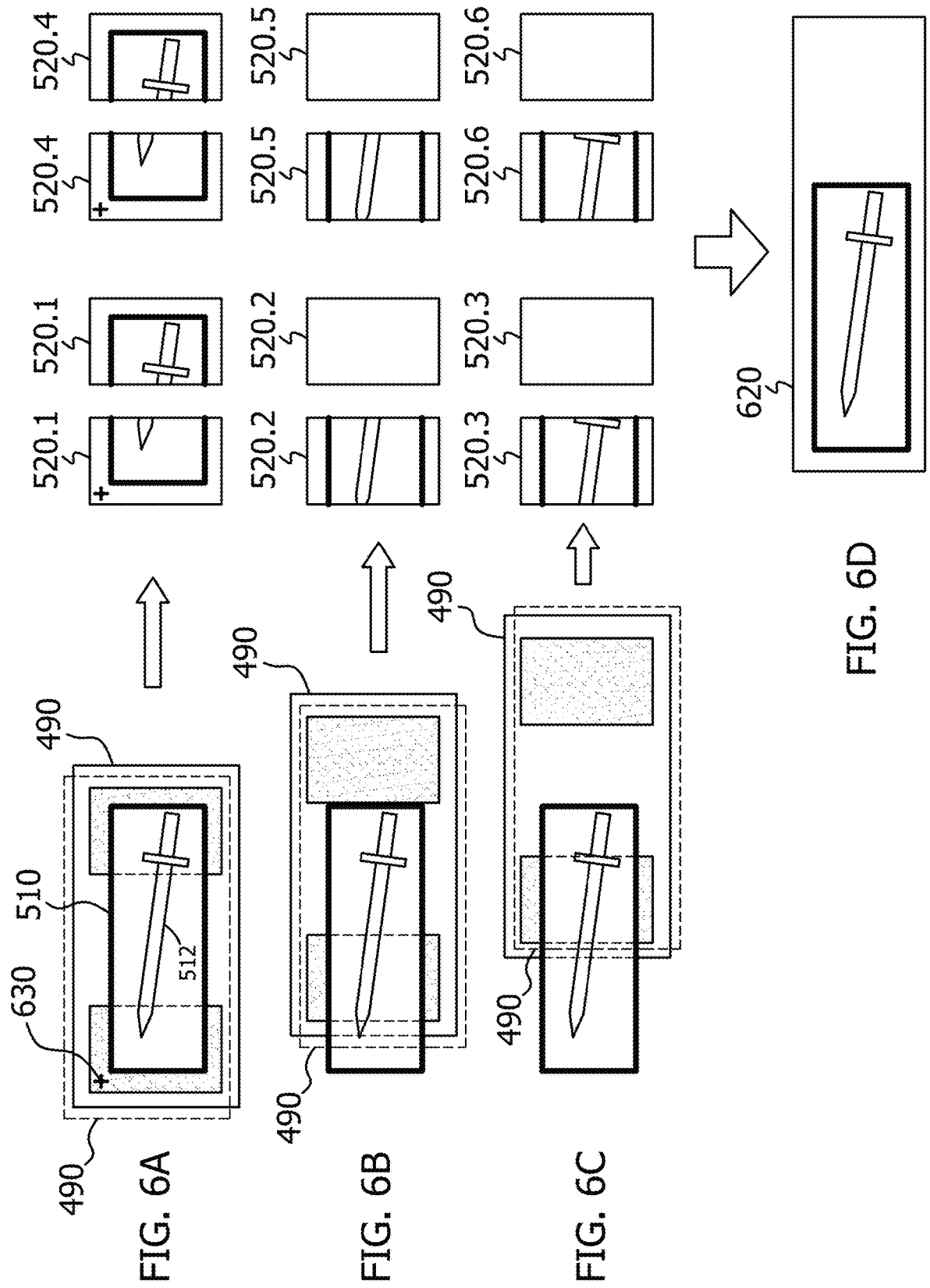
FIG. 6A-FIG. 6D schematically show top views of the image sensor in operation, according to an alternative embodiment.

In an embodiment, after capturing the third partial image 520.3, the image sensor 490 may be moved to a fourth image capture location (dashed rectangle 490 in FIG. 6A) at or near the first image capture location (solid rectangle 490 in FIG. 6A). Then, the image sensor 490 may be used to capture a fourth partial image 520.4 of the object/scene 510+512 while the image sensor 490 is at the fourth image capture location. The first and fourth image capture locations may be considered to belong to a first location group. The first and fourth partial images may be considered to belong to a first partial image group.

In an embodiment, after capturing the fourth partial image 520.4, the image sensor 490 may be moved to a fifth image capture location (dashed rectangle 490 in FIG. 6B) at or near the second image capture location (solid rectangle 490 in FIG. 6B). Then, the image sensor 490 may be used to capture a fifth partial image 520.5 of the object/scene 510+512 while the image sensor 490 is at the fifth image capture location. The second and fifth image capture locations may be considered to belong to a second location group. The second and fifth partial images may be considered to belong to a second partial image group.

In an embodiment, after capturing the fifth partial image 520.5, the image sensor 490 may be moved to a sixth image capture location (dashed rectangle 490 in FIG. 6C) at or near the third image capture location (solid rectangle 490 in FIG. 6C). Then, the image sensor 490 may be used to capture a sixth partial image 520.6 of the object/scene 510+512 while the image sensor 490 is at the sixth image capture location. The third and sixth image capture locations may be considered to belong to a third location group. The third and sixth partial images may be considered to belong to a third partial image group.

In an embodiment, the positions of the 6 image capture locations may be such that the minimum distance between an image capture location of a location group of the first, second, and third location groups and another image capture location of another location group of the first, second, and third location groups is substantially larger than (e.g., more than 10 times, more than 20 times, more than 50 times, or more than 100 times) the maximum distance between 2 image capture locations of a location group of the first, second, and third location groups. In other words, the minimum distance between 2 image capture locations of 2 different location groups is substantially larger than the maximum distance between 2 image capture locations of a same group.

In an embodiment, said minimum distance may be close to and less than the width 190w (FIG. 5A) of the sensing area 190a. For example, said minimum distance may be in the range from 80% to 99.99% of the width 190w. In an embodiment, said minimum distance may be more than 100 times said maximum distance. In an embodiment, said maximum distance may be less than 10 times the size of a sensing element 150.

In an embodiment, the image sensor 490 may only move from an image capture location of a location group directly to another image capture location of another location group. This means that in this embodiment, the image sensor 490 may not move from an image capture location of a location group directly to another image capture location of the same location group. For example, in this embodiment, the image sensor 490 may move from the third image capture location directly to the fifth image capture location because the third and fifth image capture locations belong to two different location groups (i.e., the third and second location groups, respectively). However, in this embodiment, the image sensor 490 may not move from the third image capture location directly to the sixth image capture location because the third and sixth image capture locations belong to the same location group (i.e., the third location group).

Next, in an embodiment, after the 6 partial images 520.1-6 are captured, a combined image 620 (FIG. 6D) of the object/scene 510+512 may be determined based on the 6 partial images 520.1-6 as follows. Specifically, in an embodiment, the partial images 520.1, 520.2, and 520.3 may be stitched to form a stitched image of the object/scene 510+512.

Next, in an embodiment, a first enhanced partial image may be determined for the first partial image group based on the partial images 520.1 and 520.4 of the first partial image group and then used to replace the partial image 520.1 of the stitched image. In other words, the partial image 520.4 is used to enhance the partial image 520.1 of the stitched image. More specifically, in an embodiment, the first enhanced partial image may be determined as follows. Firstly, the positions of the first and fourth image capture locations relative to each other may be determined by (A) measurement using markers or (B) estimation using inter-image correlation.

In method (A), in an embodiment, markers may be added at fixed positions relative to the object/scene 510+512 such that at least one of the markers is present in each of the partial images 520.1 and 520.4 of the first partial image group. For example, a marker 630 (FIG. 6A) is shown for illustration (other markers are not shown for simplicity) and its images are in the partial images 520.1 and 520.4. In an embodiment, the markers may have the shape of a cross (e.g., the marker 630). In an embodiment, the markers may comprise a metal such as aluminum. With the positions of the markers relative to the object/scene 510+512 known, the positions of the first and fourth image capture locations relative to each other may be measured.

Method (B), in an embodiment, may involve correlating the 2 partial images 520.1 and 520.4 to determine the positions of the first and fourth image capture locations relative to each other. Specifically, in an embodiment, two portions of the 2 partial images 520.1 and 520.4 of the first partial image group may be compared to determine a correlation coefficient. In an embodiment, if the determined correlation coefficient exceeds a pre-specified threshold, the two portions from the 2 partial images 520.1 and 520.4 may be considered identical and hence the positions of the first and fourth image capture locations (corresponding to the partial images 520.1 and 520.4 respectively) relative to each other may be estimated. In an embodiment, if the determined correlation coefficient does not exceed the pre-specified threshold, the two portions from the 2 partial images 520.1 and 520.4 may be considered non-identical, and another two portions of the 2 partial images 520.1 and 520.4 of the first partial image group may be compared, and so on.

In an embodiment, the resolutions of the 2 partial images 520.1 and 520.4 of the first partial image group may be increased (upsampling) before the correlating process described above is performed. In an embodiment, this upsampling process may be performed using interpolation.

In an embodiment, with the positions of the first and fourth image capture locations relative to each other determined as described above, a resolution enhancing algorithm (also known as a super resolution algorithm) may be applied to the 2 partial images 520.1 and 520.4 of the first partial image group to form the first enhanced partial image. In an embodiment, the first enhanced partial image may be used to replace the first partial image 520.1 in the stitched image.

In an embodiment, in a similar manner, a second enhanced partial image may be determined for the second partial image group based on the 2 partial images 520.2 and 520.5 of the group and then may be used to replace the partial image 520.2 in the stitched image. Similarly, a third enhanced partial image may be determined for the third partial image group based on the 2 partial images 520.3 and 520.6 of the group and then may be used to replace the partial image 520.3 in the stitched image. In an embodiment, after the 3 replacements as described above, if different regions of the stitched image have different resolutions, then algorithms may be performed to cause the entire stitched image to have the same resolution resulting in the combined image 620 (FIG. 6D).

FIG. 7 shows a flowchart 700 summarizing the operation of the image sensor 490 according to FIG. 6A-FIG. 6D. Specifically, in step 710, the image sensor 490 moves through different image capture locations and captures partial images while being at these image capture locations. In step 720, some of the captured partial images (e.g., one partial image from each partial image group) are stitched to form a stitched image of the scene. In step 730, for each partial image group, an enhanced partial image is determined based on the partial images of the partial image group, and the resulting enhanced partial image are used to replace the corresponding partial image of the stitched image (i.e., to enhance the stitched image). In step 740, equalization of resolutions is performed for the stitched image if necessary (i.e., if different regions of the stitched image have different resolutions) resulting in the combined image 620 of the object/scene 510+512 (FIG. 6D).

FIG. 8 shows a flowchart 800 summarizing and generalizing an operation of the image sensor 490, according to an embodiment. In step 810, the image sensor 490 may be positioned at different locations, and different partial images of a same scene may be captured with the image sensor 490 at these different locations, wherein a minimum distance between two locations of two different location groups is substantially larger than a maximum distance between two locations of a location group. In an embodiment, the image sensor 490 may be positioned at these different locations one by one (i.e. at one location after another) for capturing those partial images. In step 820, a combined image of the scene may be determined based on the captured partial images.

In the embodiments described above, with reference to FIG. 4, and FIG. 5A-FIG. 5D, the image sensor 490 comprises 2 sensing areas 190a and 190b which are physically separated from each other by the dead zone 488 and in the shape of rectangles. In general, the image sensor 490 may comprise N sensing areas 190 (N is a positive integer) which may be physically separated from each other by a dead zone (e.g., dead zone 488), may be in any size or shape, and may be arranged in any way.

In the embodiments described above, the cardboard box 510 enclosing the metal sword 512 is used as an example of the object or scene being examined. In general, any object or scene may be examined using the image sensor 490.

In the embodiments described above, the image sensor 490 comprises 2 sensing areas 190 and moves through 3 location groups of 2 image capture locations. In general, the image sensor 490 may comprise N sensing areas (N is a positive integer) and move through P location groups (P is an integer greater than 1), wherein each location group may have any number of image capture locations. As a result, the numbers of image capture locations of the location groups do not have to be the same.

In the embodiments described above, the image sensor 490 moves between the 6 image capture locations in the order of the first, second, third, fourth, fifth, and then sixth image capture locations. In general, the image sensor 490 may move between the 6 image capture locations (or any number of image capture locations) in any order. For example, the image sensor 490 may move between the 6 image capture locations in the order of the first, second, third, fifth, sixth, and then fourth image capture locations.

In the embodiments described above, the object/scene 510+512 remains stationary and the image sensor 490 moves relative to the object/scene 510+512. In general, any moving arrangement may be possible as long as the image sensor 490 moves relative to the object/scene 510+512. For example, the image sensor 490 may remain stationary and the object/scene 510+512 may move relative to the image sensor 490.

In the embodiments described above, the partial images 520.1, 520.2, and 520.3 are stitched to form the stitched image of the object/scene 510+512. In general, a combination of partial images with one partial image from each partial image group may be stitched to form a stitched image of the object/scene 510+512. For example, the partial images 520.1, 520.5, and 520.6 may be stitched to form a stitched image of the object/scene 510+512.

In the embodiments described above, stitching is performed then enhanced partial images are determined and used to enhance the stitched image. Alternatively, enhanced partial images are determined before stitching is performed. For example, the first, second, and third enhanced partial images may be determined as described above. Then, the first, second, and third enhanced partial images may be stitched to form a combined and complete image of the object/scene 510+512 (e.g., image 620 of FIG. 6D). Many other possible ways of handling the 6 partial images 520.1-6 may be used to form the combined and complete image of the object/scene 510+512.

In the embodiments described above, the first, second, and third enhanced partial images are used to replace the corresponding partial images in the stitched image. In an alternative embodiment, an enhanced partial image of a partial image group is not used for such replacement if the enhanced partial image does not have a higher resolution than that of the partial image which the enhanced partial image is supposed to replace in the stitched image.

For example, the first enhanced partial image of the first partial image group is not used to replace the partial image 520.1 of the stitched image if the first enhanced partial image does not have a higher resolution than the resolution of the partial image 520.1. This situation occurs when the distance (or offset) between the corresponding first and fourth image capture locations is K times the size of the sensing element 150, wherein K is a non-negative integer.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of using an image sensor comprising N sensing areas for capturing images of a scene, N being a positive integer, the N sensing areas being physically separate from each other, the method comprising:
    for i=1, . . . , P, and j=1, . . . , Q(i), positioning the image sensor at a location (i,j) relative to the scene and capturing a partial image (i,j) of the scene using the image sensor while the image sensor is at the location (i,j), thereby capturing in total R partial images,
    wherein R is the sum of Q(i), i=1, . . . , P,
    wherein Q(i), i=1, . . . , P are positive integers and are not all 1,
    wherein for i=1, . . . , P, a location group (i) comprises the locations (i,j), j=1, . . . , Q(i), and
    wherein a minimum distance between a location of a location group of the location groups (i), i=1, . . . , P and another location of another location group of the location groups (i), i=1, . . . , P is substantially larger than a maximum distance between two locations of a location group of the location groups (i), i=1, . . . , P; and
    determining a combined image of the scene based on the R partial images;
    wherein said determining the combined image comprises stitching the partial images (i,1), i=1, . . . , P to form a stitched image of the scene;
    wherein said determining the combined image further comprises for i=1, . . . , P determining an enhanced partial image (i) based on the partial images (i,j), j=1, . . . , Q(i);
    wherein said determining the combined image further comprises for i=1, . . . , P using the enhanced partial image (i) to replace the partial image (i,1) of the stitched image if a resolution of the enhanced partial image (i) is higher than that of the partial image (i,1).

2. The method of claim 1, wherein N is greater than 1.

3. The method of claim 1, wherein said positioning the image sensor at the locations (i,j) for i=1, . . . , P, and j=1, . . . , Q(i) are performed one by one.

4. The method of claim 1, wherein Q(i), i=1, . . . , P are the same and greater than 1.

5. The method of claim 1, wherein said minimum distance is close to and less than a size of a sensing area of the N sensing areas.

6. The method of claim 1, wherein said minimum distance is more than 100 times said maximum distance.

7. The method of claim 1, wherein said maximum distance is less than 10 times a size of a sensing element of the N sensing areas.

8. The method of claim 1, wherein said positioning the image sensor at the locations (i,j) for i=1, . . . , P, and j=1, . . . , Q(i) comprises moving the image sensor from a location of a location group of the location groups (i), i=1, . . . , P directly to another location of another location group of the location groups (i), i=1, . . . , P and does not comprise moving the image sensor from a location of a location group of the location groups (i), i=1, . . . , P directly to another location of the same location group.

9. The method of claim 1, wherein said determining the combined image further comprises for i=1, . . . , P using the enhanced partial image (i) to replace the partial image (i,1) of the stitched image.

10. The method of claim 9, wherein said determining the combined image further comprises equalizing resolutions of different regions of the stitched image after said using is performed.

11. The method of claim 1, wherein said determining the combined image further comprises equalizing resolutions of different regions of the stitched image after said using is performed.

12. The method of claim 1, wherein said determining the enhanced partial images (i) comprises determining positions of the locations (i,j), j=1, . . . , Q(i) relative to each other.

13. The method of claim 12, wherein said determining the positions of the locations (i,j), j=1, . . . , Q(i) relative to each other comprises using markers which are stationary relative to the scene.

14. The method of claim 12, wherein said determining the positions of the locations (i,j), j=1, . . . , Q(i) relative to each other comprises:
    upsampling the partial images (i,j), j=1, . . . , Q(i) resulting in upsampled partial images (i,j), j=1, . . . , Q(i) respectively; and
    correlating the upsampled partial images (i,j), j=1, . . . , Q(i) to determine the positions of the locations (i,j), j=1, . . . , Q(i) relative to each other.

15. The method of claim 1, wherein said determining the combined image comprises for i=1, . . . , P determining an enhanced partial image (i) based on the partial images (i,j), j=1, . . . , Q(i).

16. The method of claim 15, wherein said determining the combined image further comprises stitching the enhanced partial images (i), i=1, . . . , P to form a stitched image of the scene.

17. The method of claim 16, wherein said determining the combined image further comprises equalizing resolutions of different regions of the stitched image.

18. The method of claim 15, wherein said determining the enhanced partial images (i) comprises determining positions of the locations (i,j), j=1, . . . , Q(i) relative to each other.

19. The method of claim 18, wherein said determining the positions of the locations (i,j), j=1, . . . , Q(i) relative to each other comprises using markers which are stationary relative to the scene.

20. The method of claim 18, wherein said determining the positions of the locations (i,j), j=1, . . . , Q(i) relative to each other comprises:

upsampling the partial images (i,j), j=1, . . . , Q(i) resulting in upsampled partial images (i,j), j=1, . . . , Q(i) respectively; and correlating the upsampled partial images (i,j), j=1, . . . , Q(i) to determine the positions of the locations (i,j), j=1, . . . , Q(i) relative to each other.

21. A method of using an image sensor comprising N sensing areas for capturing images of a scene, N being a positive integer, the N sensing areas being physically separate from each other, the method comprising:

for i=1, . . . , P, and j=1, . . . , Q(i), positioning the image sensor at a location (i,j) relative to the scene and capturing a partial image (i,j) of the scene using the image sensor while the image sensor is at the location (i,j), thereby capturing in total R partial images, wherein R is the sum of Q(i), i=1, . . . , P, wherein Q(i), i=1, . . . , P are positive integers and are not all 1, wherein for i=1, . . . , P, a location group (i) comprises the locations (i,j), j=1, . . . , Q(i), and wherein a minimum distance between a location of a location group of the location groups (i), i=1, . . . , P and another location of another location group of the location groups (i), i=1, . . . , P is substantially larger than a maximum distance between two locations of a location group of the location groups (i), i=1, . . . , P; and determining a combined image of the scene based on the R partial images;

wherein said determining the combined image comprises stitching the partial images (i,1), i=1, . . . , P to form a stitched image of the scene;

wherein said determining the combined image further comprises for i=1, . . . , P determining an enhanced partial image (i) based on the partial images (i,j), j=1, . . . , Q(i);

wherein said determining the enhanced partial images (i) comprises determining positions of the locations (i,j), j=1, . . . , Q(i) relative to each other;

wherein said determining the positions of the locations (i,j), j=1, . . . , Q(i) relative to each other comprises:

upsampling the partial images (i,j), j=1, . . . , Q(i) resulting in upsampled partial images (i,j), j=1, . . . , Q(i) respectively; and correlating the upsampled partial images (i,j), j=1, . . . , Q(i) to determine the positions of the locations (i,j), j=1, . . . , Q(i) relative to each other.

22. The method of claim 21, wherein N is greater than 1.

23. The method of claim 21, wherein said positioning the image sensor at the locations (i,j) for i=1, . . . , P, and j=1, . . . , Q(i) are performed one by one.

24. The method of claim 21, wherein Q(i), i=1, . . . , P are the same and greater than 1.

25. The method of claim 21, wherein said minimum distance is close to and less than a size of a sensing area of the N sensing areas.

26. The method of claim 21, wherein said minimum distance is more than 100 times said maximum distance.

27. The method of claim 21, wherein said maximum distance is less than 10 times a size of a sensing element of the N sensing areas.

28. The method of claim 21, wherein said positioning the image sensor at the locations (i,j) for i=1, . . . , P, and j=1, . . . , Q(i) comprises moving the image sensor from a location of a location group of the location groups (i), i=1, . . . , P directly to another location of another location group of the location groups (i), i=1, . . . , P and does not comprise moving the image sensor from a location of a location group of the location groups (i), i=1, . . . , P directly to another location of the same location group.

29. The method of claim 21, wherein said determining the combined image further comprises for i=1, . . . , P using the enhanced partial image (i) to replace the partial image (i,1) of the stitched image.

30. The method of claim 29, wherein said determining the combined image further comprises equalizing resolutions of different regions of the stitched image after said using is performed.

31. The method of claim 21, wherein said determining the positions of the locations (i,j), j=1, . . . , Q(i) relative to each other comprises using markers which are stationary relative to the scene.

32. The method of claim 21, wherein said determining the combined image comprises for i=1, . . . , P determining an enhanced partial image (i) based on the partial images (i,j), j=1, . . . , Q(i).

33. The method of claim 32, wherein said determining the combined image further comprises stitching the enhanced partial images (i), i=1, . . . , P to form a stitched image of the scene.

34. The method of claim 33, wherein said determining the combined image further comprises equalizing resolutions of different regions of the stitched image.

35. The method of claim 32, wherein said determining the enhanced partial images (i) comprises determining positions of the locations (i,j), j=1, . . . , Q(i) relative to each other.

36. The method of claim 35, wherein said determining the positions of the locations (i,j), j=1, . . . , Q(i) relative to each other comprises using markers which are stationary relative to the scene.

37. The method of claim 35, wherein said determining the positions of the locations (i,j), j=1, . . . , Q(i) relative to each other comprises:

upsampling the partial images (i,j), j=1, . . . , Q(i) resulting in upsampled partial images (i,j), j=1, . . . , Q(i) respectively; and correlating the upsampled partial images (i,j), j=1, . . . , Q(i) to determine the positions of the locations (i,j), j=1, . . . , Q(i) relative to each other.

38. A method of using an image sensor comprising N sensing areas for capturing images of a scene, N being a positive integer, the N sensing areas being physically separate from each other, the method comprising:

for i=1, . . . , P, and j=1, . . . , Q(i), positioning the image sensor at a location (i,j) relative to the scene and capturing a partial image (i,j) of the scene using the image sensor while the image sensor is at the location (i,j), thereby capturing in total R partial images, wherein R is the sum of Q(i), i=1, . . . , P, wherein Q(i), i=1, . . . , P are positive integers and are not all 1, wherein for i=1, . . . , P, a location group (i) comprises the locations (i,j), j=1, . . . , Q(i), and wherein a minimum distance between a location of a location group of the location groups (i), i=1, . . . , P and another location of another location group of the location groups (i), i=1, . . . , P is substantially larger than a maximum distance between two locations of a location group of the location groups (i), i=1, . . . , P; and determining a combined image of the scene based on the R partial images;

wherein said determining the combined image comprises for i=1, . . . , P determining an enhanced partial image (i) based on the partial images (i,j), j=1, . . . , Q(i);

wherein said determining the enhanced partial images (i) comprises determining positions of the locations (i,j), j=1, . . . , Q(i) relative to each other;

wherein said determining the positions of the locations (i,j), j=1, . . . , Q(i) relative to each other comprises:

upsampling the partial images (i,j), j=1, . . . , Q(i) resulting in upsampled partial images (i,j), j=1, . . . , Q(i) respectively; and correlating the upsampled partial images (i,j), j=1, . . . , Q(i) to determine the positions of the locations (i,j), j=1, . . . , Q(i) relative to each other.

39. The method of claim 38, wherein N is greater than 1.

40. The method of claim 38, wherein said positioning the image sensor at the locations (i,j) for i=1, . . . , P, and j=1, . . . , Q(i) are performed one by one.

41. The method of claim 38, wherein Q(i), i=1, . . . , P are the same and greater than 1.

42. The method of claim 38, wherein said minimum distance is close to and less than a size of a sensing area of the N sensing areas.

43. The method of claim 38, wherein said minimum distance is more than 100 times said maximum distance.

44. The method of claim 38, wherein said maximum distance is less than 10 times a size of a sensing element of the N sensing areas.

45. The method of claim 38, wherein said positioning the image sensor at the locations (i,j) for i=1, . . . , P, and j=1, . . . , Q(i) comprises moving the image sensor from a location of a location group of the location groups (i), i=1, . . . , P directly to another location of another location group of the location groups (i), i=1, . . . , P and does not comprise moving the image sensor from a location of a location group of the location groups (i), i=1, . . . , P directly to another location of the same location group.

46. The method of claim 38, wherein said determining the combined image comprises stitching the partial images (i,1), i=1, . . . , P to form a stitched image of the scene.

47. The method of claim 46, wherein said determining the combined image further comprises for i=1, . . . , P determining an enhanced partial image (i) based on the partial images (i,j), j=1, . . . , Q(i).

48. The method of claim 47, wherein said determining the combined image further comprises for i=1, . . . , P using the enhanced partial image (i) to replace the partial image (i,1) of the stitched image.

49. The method of claim 48, wherein said determining the combined image further comprises equalizing resolutions of different regions of the stitched image after said using is performed.

50. The method of claim 47, wherein said determining the enhanced partial images (i) comprises determining positions of the locations (i,j), j=1, . . . , Q(i) relative to each other.

51. The method of claim 50, wherein said determining the positions of the locations (i,j), j=1, . . . , Q(i) relative to each other comprises using markers which are stationary relative to the scene.

52. The method of claim 38, wherein said determining the combined image further comprises stitching the enhanced partial images (i), i=1, . . . , P to form a stitched image of the scene.

53. The method of claim 52, wherein said determining the combined image further comprises equalizing resolutions of different regions of the stitched image.

54. The method of claim 38, wherein said determining the positions of the locations (i,j), j=1, . . . , Q(i) relative to each other comprises using markers which are stationary relative to the scene.

* * * * *